(12) United States Patent
Kühn et al.

(10) Patent No.: US 11,992,614 B2
(45) Date of Patent: May 28, 2024

(54) RESPIRATORY DEVICE

(71) Applicant: HAMILTON MEDICAL AG, Bonaduz (CH)

(72) Inventors: Lars Kühn, Grüsch (CH); Dominik Novotni, Chur (CH); Thomas Laubscher, Rhäzüns (CH)

(73) Assignee: HAMILTON MEDICAL AG, Bonaduz (CH)

( * ) Notice: Subject to any disclaimer, the term of this patent is extended or adjusted under 35 U.S.C. 154(b) by 703 days.

(21) Appl. No.: 15/553,520

(22) PCT Filed: Feb. 15, 2016

(86) PCT No.: PCT/EP2016/053189
§ 371 (c)(1),
(2) Date: Aug. 24, 2017

(87) PCT Pub. No.: WO2016/134999
PCT Pub. Date: Sep. 1, 2016

(65) Prior Publication Data
US 2018/0221609 A1 Aug. 9, 2018

(30) Foreign Application Priority Data
Feb. 26, 2015 (DE) .................... 10 2015 203 455.0

(51) Int. Cl.
A61M 16/00 (2006.01)
G16H 40/63 (2018.01)

(52) U.S. Cl.
CPC ........ *A61M 16/026* (2017.08); *A61M 16/024* (2017.08); *G16H 40/63* (2018.01);
(Continued)

(58) Field of Classification Search
CPC .............. A61M 16/026; A61M 16/024; A61M 16/022; A61M 2205/3331;
(Continued)

(56) References Cited

U.S. PATENT DOCUMENTS 4,986,268 A * 1/1991 Tehrani ................ A61M 16/00
128/204.22
5,129,390 A * 7/1992 Chopin ............... A61M 16/024
128/204.26
(Continued)

FOREIGN PATENT DOCUMENTS

CN 103908713 7/2014
EP 1 984 050 B1 10/2010
(Continued)

OTHER PUBLICATIONS

Otis, Fenn, Rahn; Mechanics of Breathing in Man; May 1950; Journal of Applied Physiology; vol. 2 Issue 11; pp. 592-607 (Year: 1950).*
(Continued)

Primary Examiner — Annette Dixon
(74) Attorney, Agent, or Firm — Tollefson IP

(57) ABSTRACT

A control system of a respiratory device for the at least supportive-partial artificial respiration of patients, in particular human patients, comprising a respiratory gas conduit arrangement, a pressure changing arrangement for changing the pressure of respiratory gas in the respiratory gas conduit arrangement during the respiratory operation of the respiratory device, and the control system for controlling the respiratory operation of the respiratory device. The control system has a data input for transmitting operational or/and patient data to the control system. The control system is configured to determine a respiratory operating parameter for the operation of the respiratory device selectively by means of a predetermined first data relationship or by means
(Continued)

Figure 1:
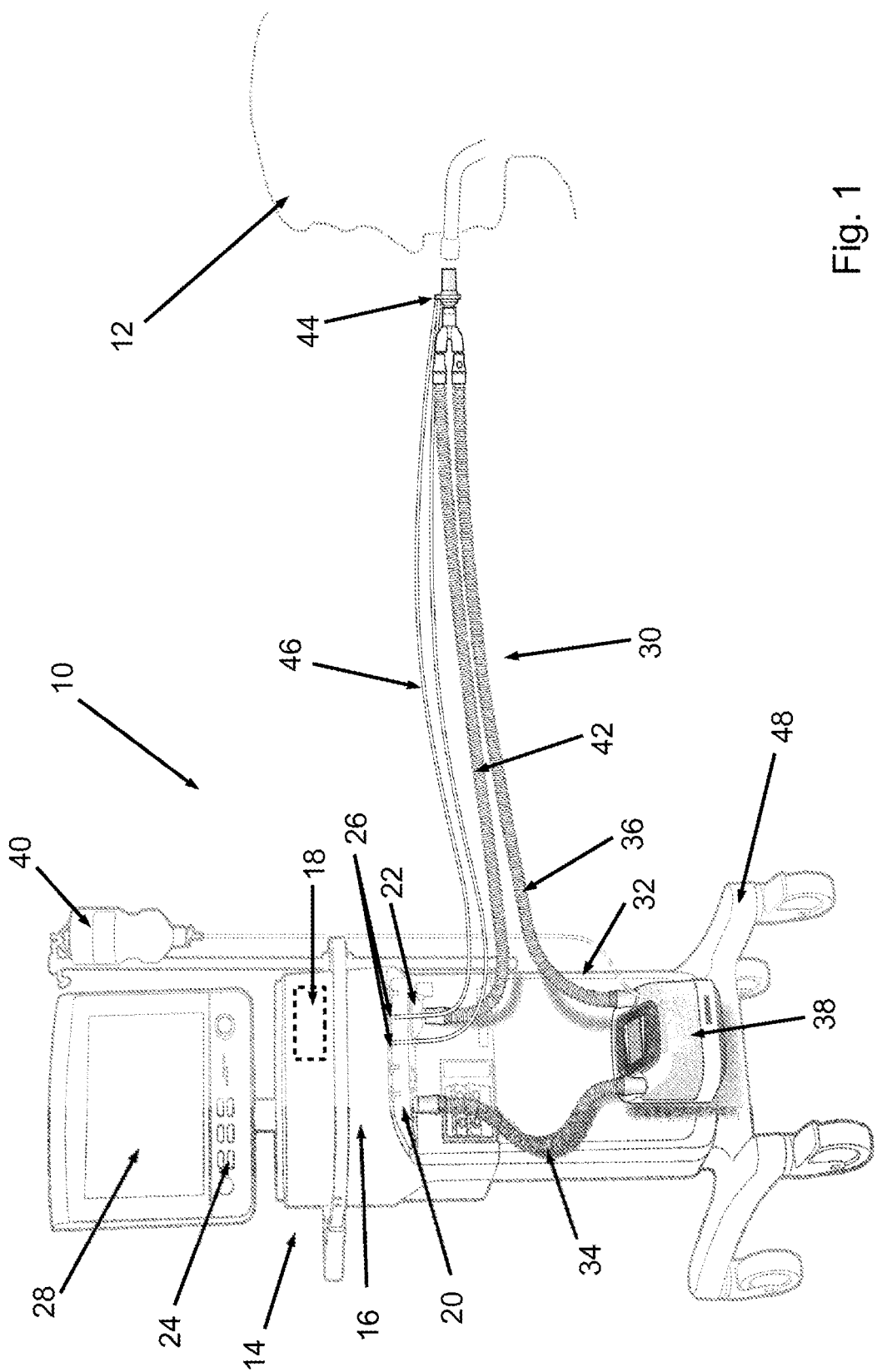

of a predetermined second data relationship that is different from the first data relationship.

25 Claims, 4 Drawing Sheets

(52) U.S. Cl.
CPC ............... *A61M 2016/0027* (2013.01); *A61M 2205/3331* (2013.01); *A61M 2205/50* (2013.01); *A61M 2230/46* (2013.01)

(58) Field of Classification Search
CPC ...... A61M 2205/3334; A61M 2230/40; A61M 2230/42; A61M 2230/46; A61M 16/0051; A61M 16/0069; A61M 16/202; A61M 16/204; A61M 16/205; A61M 2005/14208; A61M 2016/0021; A61M 2016/0027; A61M 2016/0039; A61M 2205/15; A61M 2205/3365; A61M 2205/50; A61M 2205/52; A61M 2230/005; A61M 2230/202; A61M 2230/205; A61B 5/0002; A61B 5/01; A61B 5/02055; A61B 5/05; A61B 5/1106; A61B 5/4821; A61B 5/72; A61B 5/746; G05B 17/02; G16H 40/63; G16H 50/50; G16Z 99/00; Y02A 90/10

See application file for complete search history.

(56) References Cited

U.S. PATENT DOCUMENTS

| | | | | |
|---|---|---|---|---|
| 5,551,419 | A * | 9/1996 | Froehlich | A61M 16/0069 |
| | | | | 128/204.26 |
| 5,752,509 | A * | 5/1998 | Lachmann | A61M 16/024 |
| | | | | 128/203.14 |
| 8,695,593 | B2 * | 4/2014 | Tehrani | A61H 31/02 |
| | | | | 128/204.26 |
| 2009/0007915 | A1 * | 1/2009 | Brunner | A61M 16/0051 |
| | | | | 128/204.23 |
| 2009/0036790 | A1 * | 2/2009 | Landesberg | A61M 16/0069 |
| | | | | 600/529 |
| 2010/0236553 | A1 * | 9/2010 | Jafari | A61M 16/0875 |
| | | | | 128/204.21 |
| 2012/0272961 | A1 | 11/2012 | Masic et al. | |
| 2012/0298108 | A1 * | 11/2012 | Kane | A61M 16/0066 |
| | | | | 128/204.23 |
| 2013/0074844 | A1 * | 3/2013 | Kimm | A61M 16/024 |
| | | | | 128/204.23 |
| 2015/0045687 | A1 * | 2/2015 | Nakai | A61B 5/085 |
| | | | | 600/533 |
| 2017/0255756 | A1 * | 9/2017 | Karbing | A61M 16/026 |

FOREIGN PATENT DOCUMENTS

| | | | |
|---|---|---|---|
| WO | 2007/085108 A1 | 8/2007 | |
| WO | WO-2008031208 A1 * | 3/2008 | ............... A61B 5/05 |
| WO | 2013/045563 A1 | 4/2013 | |

OTHER PUBLICATIONS

Mead; Control of Respiratory Frequency; May 1960; Journal of Applied Physiology; vol. 15 Issue 3; pp. 325-336 (Year: 1960).*

Fernández, Miguelena, Mulett, Godoy, Martinón-Torres; Adaptive support ventilation: State of the art review; Jan. 2013; Indian Journal of Critical Care Medicine; vol. 17 Issue 1; 16-22 (Year: 2013).*

"Average.", Apr. 6, 2020, Merriam-Webster.com Dictionary, Merriam-Webster, https://www.merriam-webster.com/dictionary/average. Accessed Apr. 14, 2020. (Year: 2020).*

Chinese Office Action issued in CN201680011962.4, dated Jun. 24, 2019.

Search Report issued for German Patent Application No. 10 2015 203 455.0 dated Oct. 13, 2015, with machine English translation 17 pages.

Search Report and Written Opinion issued for International Patent Application No. PCT/EP2016/053189 dated Apr. 18, 2016, 10 pages.

Brunner et al. "Simple method to measure total expiratory time constant based on the passive expiratory flow-volume curve"; Jun. 1995, Critical Care Medicine, vol. 23, No. 6.

Lourens et al. "Expiratory time constants in mechanically ventilated patients with and without COPD"; Oct. 31, 2000, Intensive Care Medicine, vol. 26, pp. 1612-1618.

* cited by examiner

RESPIRATORY DEVICE

CROSS-REFERENCE TO RELATED APPLICATIONS

This application is a 35 U.S.C. § 371 National Phase Entry Application from PCT/EP2016/053189, filed on Feb. 15, 2016, and designating the United States, which claims priority under 35 U.S.C. § 119 to German Patent Application No. 10 2015 203 455.0, filed on Feb. 26, 2015, the entire disclosures of which are incorporated herein by reference.

The present invention relates to a respiratory device for the at least supportive-partial artificial respiration of patients, in particular of human patients. The respiratory device includes a respiratory gas conduit assembly, a pressure changing assembly and a control device. The pressure changing assembly is used for changing the pressure of respiratory gas in the respiratory gas conduit assembly during the respiratory operation of the respiratory device. The control device is used to control the operation of the respiratory device, in particular of the pressure changing assembly. The control device has a data input for the transfer of operating data and/or of patient data to the control device. It is configured to determine a respiratory operating parameter for the operation of the respiratory device, in particular of the pressure changing assembly, selectively using a predetermined first data relationship or using a predetermined second data relationship that is different from the first data relationship.

Respiratory devices of this kind are known from clinical applications, such as in surgery or in intensive medicine, for artificial respiration of persons. The respiratory devices can be employed for full ventilation of persons who are no longer able to do so by their own efforts. Among such persons are patients with narcotized respiratory system or comatose patients. Therefore in addition to intensive respiratory devices, the present application relates also, but not only, to anesthesia respiratory devices. However, respiratory devices of the kind described above can also be used for supportive respiration of persons who are able to breathe to a certain extent under their own efforts, but who cannot independently fully cover their requirement for respiratory gas.

In addition to human medicine, respiratory devices of the present invention are also being used in veterinary medicine, such as for respiration of animals during narcosis phases. Animals treated under such circumstances in veterinary medicine should also be viewed as "patients" within the meaning of the present application.

Respiratory gas is directed to the patient, in particular to the patient's respiratory organs, using the respiration gas conduit assembly. The respiration gas conduit assembly can also be used, at least in sections, for the venting of consumed, metabolized respiration gas from the patients into the atmosphere. The respiratory gas conduit assembly comprises at least one respiration gas conduit, such as a hose, and at least one valve for selection of flow paths for the inspiration and exhalation.

The respiratory gas flow in the respiratory gas conduit assembly required for artificial respiration of patients is effected by the pressure changing arrangement which is configured to change the pressure of the respiratory gas in the respiratory gas conduit assembly, and thus to generate pressure differences between a respiratory gas volume outside of the patient's body and a gas pressure in the interior of the respiratory organs of the patient, and thereby to create a respiratory gas flow to or from the respiratory organs of the patient. Usually the pressure changing assembly consists of a pump, a ventilator fan or a compressor and similar items for manipulation of the pressure of the respiration gas in the respiratory gas conduit assembly.

The pressure changing assembly can also comprise a reducing valve. For example, the reducing valve connected to an installed respiration gas pressure reservoir, like that frequently encountered in clinics as the central respiratory gas supply installation, can serve as the pressure changing arrangement within the meaning of the present invention. Due to the reducing valve, the pressure of the respiration gas which can be tapped from the respiratory gas supply installation at tap stations in treatment and/or patient rooms can be reduced to a pressure range suitable for artificial respiration, for example, to an over-pressure maximum of about 30 mbar.

Operation of the respiratory device, in particular of the pressure changing assembly, but also of valves of the respiratory gas conduit assembly, during the respiratory operation is controlled by the control device. With the control device, at least one respiratory operating parameter can be determined for operation of the pressure changing assembly selectively suing a first data relationship or a second data relationship, which are each predetermined.

A respiratory device of the above-described type is known from WO 2007/085108 A. This publication, whose object quite in general is the providing of an optimum respiration of a patient, teaches, among other things, the calculation of a tidal volume and of a suitable respiratory frequency as respiratory operating parameters, depending on a not specifically defined activity of the patient to be artificially ventilated, either according to the known formula of Otis or according to the known formula of Mead as the previously known data relationships. The publication mentioned, however, says nothing about according to which criteria, and dependent on which activity, the one or the other formula is to be used.

Basically the Otis and Mead calculation formulas have been used for decades as the basis for calculation of respiratory operating parameters. Since respiratory devices satisfy not only functions of sustaining life in medical therapy, but rather also can have a severely adverse effect on the particular patient under treatment in terms of an insufficient respiratory supply if the respiratory operating parameters are improperly selected, the experts—in particular medical personnel working with the respiratory devices on the patient— have been exceptionally reluctant to apply calculation formulas other than the proven Otis or Mead formulas stated above. It has long been known that they are suitable for the proper operation of respiratory devices.

From WO 2013/045563 A1 a respiratory tube system is known which also can be used with the present invention as respiratory gas conduit assembly.

The object of the present invention is to improve the respiratory device specified above, in particular to the effect that it can be tailored more precisely to the actual respiratory gas requirement of a patient.

This object is achieved according to the invention by a generic respiratory device wherein the control device is configured to determine the respiratory operating parameter for a specific respiratory gas requirement, depending on a resistance data value denoting a respiration resistance of a patient to be ventilated, according to the first data relationship or according to the second data relationship.

The idea preferably is that the control device is configured to select a data relationship from the predetermined first and the predetermined second data relationship depending on a resistance data value denoting a respiration resistance in connection with a patient to be ventilated, and thus to determine the respiratory operating parameter from the first data relationship and the second data relationship for a specific respiratory gas requirement, subject to the selected data relationship.

A respiratory operating parameter within the meaning of the present application is a parameter which is adjusted for operation of the respiratory device, in particular of the pressure changing assembly. "Patient data" means data which describe the patient to be ventilated, such as body weight, body height, clinical picture, age, gender, body mass index, fitness and the like.

Basically an artificial respiration always proceeds against the internal system respiratory resistance of the respiratory device and of the patient. The respiratory device must supply work against this respiratory resistance in order to supply the patient's alveoli with sufficient, fresh respiration gas. Of course, it is also possible to supply work against the respiratory resistance to remove the consumed respiratory gas from the alveoli, but preferably only the supply of fresh respiratory gas to the patient's alveoli (inspiration) from the respiratory device is supported. The exhalation (expiration) is usually effected solely due to the increased body tension of the patient's respiratory apparatus, which was increased during the immediately preceding inspiration phase due to the gas introduced into the body. Thus after closing of the inspiration valve, by which an inspiration tube bringing fresh respiratory gas to the patient is blocked, in general an exhalation valve is opened, so that the body tension of the respiratory apparatus of the patient can relax through exhalation of consumed respiratory gas to the atmosphere.

The respiratory resistance to be overcome in the particular respiratory case is different in each case. Since the respiratory device normally uses standardized components, in particular for the respiratory gas conduit assembly, differences in the respiratory resistance between two different patients ventilated with the same respiratory device will depend essentially on the patients. Depending on the particular condition of the patient, the respiratory resistance can be caused largely by the patient. Nonetheless, at this point it should be mentioned that the components of the respiratory device carrying the respiratory gas also make a contribution to the respiratory resistance. Potentially, the contribution of the respiratory device to the respiratory resistance in the individual case or in a class of cases can be left out of consideration in comparison to the contribution of the patient to the respiratory resistance, without this simplification resulting in too great a deviation from reality.

The wording "respiratory resistance in connection with a patient to be ventilated" is intended to express that basically the total respiratory resistance to be overcome by the artificial respiration is the definitive matter, even though—as stated above—it can be simplified under certain, permissible circumstances. The expression used is equivalent to the respiratory resistance in the particular respiratory case.

The requirement for respiratory gas of a patient is obtained from the metabolism which needs the respiratory gas for oxidation. The requirement for respiratory gas can be stated as the tidal volume, that is, the volume of respiratory gas in one breath, multiplied by the respiration frequency; that is, the number of repetitions of breath inhalations during a specified period of time, usually 1 minute.

A consistent respiratory gas requirement can be obtained using different pairs of tidal volume and respiration frequency. An increase in the one value requires a reciprocal decrease in the other value.

There are different clinically accepted guideline values with regard to the particular, suitable tidal volume for different patient conditions, such as clinical picture, level of sedation, exhaustion and the like, and patient constitutions, such as gender, body structure, muscle mass, fitness and the like. However, these factors can only provide a rough orientation, since in many cases the treatment will be greatly affected by the individual physical and health circumstances of the particular patient.

As one component, the respiratory resistance can comprise a flow resistance, caused for example, by friction of the respiratory gas against the tube walls carrying the respiratory gas, and by turbulences in the respiratory gas flow, and as an alternative or additional component, it may comprise a body resistance, caused for example, by the deformation of the tubes carrying the respiratory gas and of the patient's body during introduction of the respiratory gas into the patient's body. Depending on the condition and constitution of the particular patient, a different weighting of the particular constituents of the respiratory resistance will be needed.

It turns out that the fundamentally accepted and proven formulas by Otis and Mead—and in fact these are the only formulas recognized among experts—can result in different values, including considerably different values for one and the same respiratory operating parameter for one and the same patient in one and the same condition. According to the most recent studies by the applicant, it is surprisingly not so much a matter of the activity of the particular patient, but rather more of the respiratory resistance caused in the patient during the artificial respiration.

Therefore the respiratory resistance in connection with the particular patient is probably the most suitable parameter for selecting one of two predetermined data relationships for determining the most suitable respiratory operating parameters for the particular patient and his specific respiratory gas requirement.

Of course, the respiratory operating parameters determined according to Otis and Mead are always in the permissible range. Nonetheless, in an individual case the respiratory operating parameters calculated according to the one formula can be more advantageous than the respiratory operating parameters calculated according to the other formula.

Even though the discussion herein is repeatedly based on these formulas due to the paramount significance of the Otis and Mead formulas, the inventive respiratory device is not limited to these formulas as the predetermined data relationships. Basically the idea of the present invention consists in selecting from a predetermined first data relationship and a predetermined second data relationship, which of them which is most suitable for the specific therapy situation, or rather, selecting the one which leads to the most suitable respiratory operating parameters.

This also includes specifically the possibility attained by the present invention of meeting the respiratory requirement of one and the same patient with one and the same respiratory gas requirement using the invented respiratory device at different times with respiratory operating parameters determined according to different data relationships, if the respiratory resistance to be overcome during the ventilation changes sufficiently. The change in respiratory resistance can occur, for example, due to partial recuperation or through pharmaceutical administration. Even a mere shift in position of the patient can cause a change in the respiratory resistance. In this respect the patient can exhibit the same activity throughout the course of the artificial respiration, such as when the patient remains in a coma. According to the present invention, the control device is thus configured in particular to determine the respiratory operating parameter for a particular respiratory gas requirement exclusively as a function of the resistance data value which denotes a respiratory resistance in connection with the patient to be ventilated, and independently of the patient's own activity, in particular independently of a patient's respiratory activity, according to the first data relationship or according to the second data relationship.

The particular respiratory resistance as related to the patient to be ventilated is represented preferably by one of these indicated resistance data values, which can be assigned in tables and graphs to values of other quantities, or even to the data relationships.

Basically it can be imagined to input data into the control device via the mentioned data input. For example, the resistance data value can also be input manually by the treating physician via the data input into the control device. In this case, the data input can be connected or connectable to a suitable input device, such as a keyboard.

But preferably the respiratory device is designed to determine the resistance data value as related to the particular patient to be ventilated. In this regard the respiratory device can detect operating parameters, such as the temporal change in the pressure changing assembly. Additionally or alternatively, the respiratory device can be connected to one or to a plurality of sensors for data transmission, which are configured to detect operating parameters of the pressure changing assembly and/or of the respiratory gas conduit assembly. The data acquired by these sensors can then be supplied via the data input to the control device, which can determine the present resistance data value in connection with the patient to be ventilated, according to known calculation models using the data values acquired by the sensors.

Since as was already mentioned above, the respiratory resistance and thus the resistance data value associated with it can change over time, and in all probability will change over time, the respiratory device according to one favorable further development of the present invention is designed so as to determine the resistance data value repeatedly in order to operate the respiratory device, or more precisely its pressure changing assembly, with the most current data and respiratory operating parameters derived therefrom.

It is particularly preferred to configure the respiratory device so as to determine the resistance data value after each, or for each respiratory cycle, so that the required respiratory operating parameter for each following respiration cycle will be available in the most updated manner.

The determining of the respiratory operating parameter using the first or of the second data relationship can be a simple step that uses a formula based on a set of predetermined input data. The determining of this respiratory operating parameter, however, can also proceed via a plurality of calculation steps. For example, the respiratory device can be designed to determine a first respiratory operating parameter for one resistance data value according to a predetermined, first data base relationship, and to determine a second respiratory base operating parameter according to a predetermined, second data base relationship different from the first one. The respiratory device can also be configured to compare the first and the second respiratory base operating parameters with each other, and depending on the result of this comparison, to determine the respiratory operating parameter using the predetermined first data relationship or using the predetermined second data relationship.

In order to be able to use the already determined respiratory base operating parameter for further determination of the respiratory operating parameter, it is advantageous if the first data relationship is a function. This function of the first and/or of the second data base relationship is equivalent to a function of the first respiratory base operating parameter and/or of the second respiratory base operating parameter leading to the same respiratory operating parameter. For example, the first data relationship can be an average value of the function forming the first and the second data base relationship. In turn, this is equivalent to an average value of the function forming the first and the second respiratory base operating parameter. Basically the named average value can be any kind of average value, that is, an arithmetic, geometric or harmonic average value. For applications in the field of artificial respiration however, an arithmetic average value has proven to be particularly helpful.

Correspondingly also for the second data relationship, *mutatis mutandis*, which likewise can be a function of the first and/or of the second data base relationship, and in particular can be a function forming an average value from the first and the second data base relationship. The discussion above relating to the average value in connection with the first data relationship applies likewise to the second data relationship. Here too, a function of the first respiratory base operating parameter and of the second respiratory base operating parameter leading to the same respiratory operating parameter is equivalent to a function of the first and/or of the second data base relationship. In one simple, but advantageous solution, the second data relationship can be the second data base relationship, so that the second respiratory base operating parameter is the respiratory operating parameter, when the latter is determined via the second data relationship.

Then when both data relationships are each functions of the first and/or of the second data base relationship, they are different functions of the first and/or of the second data base relationship in order to be able to determine a most suitable and best-possible, respiratory operating parameter adapted to the patient to be ventilated, as a function of the respiratory resistance to be overcome.

The comparison that the respiratory device carries out on the first and on the second respiratory base operating parameter can basically be any kind of comparison, even a multiple step comparison, in which several values derived from the particular respiratory base operating parameters can be compared to each other.

A particularly preferred solution is a simple one that requires little computational effort and is fast to complete, wherein the respiratory device is configured such that when the first respiratory base operating parameter is greater than the second respiratory base operating parameter, an average value of the first and of the second respiratory base operating parameter is used as the respiratory operating parameter, and when the first respiratory base operating parameter is less than the second respiratory base operating parameter or is equal to the respiratory base operating parameter, the second respiratory base operating parameter is used as the respiratory operating parameter.

In turn the average value is preferably an arithmetic average value, even though the other average values stated above should not be excluded.

In addition or alternatively, a data relationship can be selected from a predetermined first and second data relationship to determine a respiratory operating parameter depending on a threshold resistance data value, if there exists one threshold resistance data value for at least a portion of the respiratory gas requirements selectable and/or adjustable on the respiratory device. Then, if such threshold resistance data values exist, for selection of the data relationship the control device can be configured such that when the resistance data value of the patient to be ventilated is below the threshold resistance data value, the respiratory device determines the respiration operating parameter according to the first data relationship, and when the resistance data value of the concrete patient is above the threshold resistance data value, the respiratory device determines the respiration operating parameter according to the second data relationship.

In turn, preferably the first data relationship can be a function of a first and/or of a second data base relationship, and the second data relationship can be a function of a first and/or of a second data base relationship different from the first data relationship.

The threshold resistance data values can be determined based on completed experiments. For example, a resistance data value can be determined as a threshold resistance data value if for smaller resistance data values the one data relationship from the first and the second data relationship yields a respiratory operating parameter better adapted to the patient to be ventilated, and if for larger resistance data values, the other data relationship yields the better adapted respiratory operating parameter. The clinically accepted guideline values described above can be used as aids in deciding which respiratory operating parameter is the more suitable one. That data relationship which yields a respiratory operating parameter for the given respiratory gas requirement of a given patient that, under consideration of the overall circumstances, is closer to the clinically accepted guideline value for the particular patient, is the more suitable value in cases of uncertainty.

A threshold resistance data value for a given respiratory gas requirement can also be obtained at an intersection of the graphs of the first and of the second data relationships as respective functions of the respiratory operating parameter dependent on the possible resistance data values. At this intersection, the first and the second data relationship for the given respiratory gas requirement of the concrete patient, that is, with otherwise the same operating and patient data, provide the same value for the respiratory operating parameter. Consequently, at this point of intersection it makes no difference whether the first or the second data relationship is used to determine the respiratory operating parameter, since the result is the same. In a range of values located on one side of the point of intersection, and thus on one side of the threshold resistance data value, toward smaller resistance values, the one data relationship can provide more favorable respiratory operating parameters, and the other data relationship can provide better respiratory operating parameters in a range of values located on the other side of the point of intersection.

As is generally commonplace in respiratory devices, preferably the respiratory operating parameter is a respiration tidal volume or a respiration frequency. With a known respiratory gas requirement, stated for example as a volume per minute, thus as the respiratory gas volume supplied to the patient during one minute—and the present invention presumes the respiratory gas requirement as predetermined—the respiration tidal volume can be calculated at known respiration frequency and the respiration frequency can be calculated at known respiration tidal volume, since the volume per minute is the product of the respiration tidal volume and the respiration frequency. Preferably the respiratory gas requirement is thus a volume per minute, and quite preferably is stated in percent volume per minute, since the known percentage value of the volume per minute can be used to make very simple conversions to other volumes per minute, such as when the condition of the patient and the patient's respiratory gas requirement change during the therapy. Other respiratory operating parameters can be, for example, the peak over-pressure value which is reached in the respiration gas during an inspiration phase, the positive end-expiratory pressure (PEEP), the relative humidity of the respiration gas, the temperature of the respiration gas and similar factors.

It was already explained above which specific types of resistance can contribute to the respiratory resistance in connection with the patient. As a consequence of this physical fact, the resistance data value can take into account a flow resistance value (known as the "resistance") of the respiratory pathway of the patient to be ventilated and/or of the conduits of the respiratory device carrying the respiratory gas. Any valves present in a conduit are deemed to be a part of the conduit. In the theoretically possible, albeit improbable case that the flow resistance accounts for the greatly predominant portion of the total resistance of the respiration, under certain circumstances it may be sufficient to take into account solely the flow resistance value (resistance) of the respiration or of the patient as the resistance data value.

In addition or alternatively, the resistance data value can take into account a flexibility value (known as the "compliance") of the respiratory organs of the patient to be ventilated and/or of the conduits of the respiratory device carrying the respiratory gas. Again, in the theoretically possible, albeit improbable case that the flexibility value accounts for the greatly predominant portion of the total resistance of the respiration, it may be sufficient to take into account solely the flexibility value as the resistance data value.

A quite realistic picture of the respiratory resistance of the concrete respiratory case, that is, of the respiratory resistance in connection with a patient, is obtained when the resistance data value denoting this resistance value takes into account both the resistance and the compliance of the actual respiratory case. Therefore, the resistance data value preferably takes into account a respiratory time constant formed as the product of the resistance and the compliance of the respiratory case. "Takes into account" means herein that the stated value or the stated values are input into the determination of the resistance data value, wherein it should not be precluded that additional values may likewise play a role in the determination of the resistance data value. However, most preferably the resistance data value is the respiratory time constant frequently used in the prior art for this purpose, and is the product of the resistance and compliance.

To determine a respiratory operating parameter, in particular for the concrete examples of a respiratory operating parameter as stated above, there are different approaches among experts, which are all based on different hypotheses. For example, a data base relationship can be based on a first and second data base relationship, or a data relationship from a first and second data relationship can be based on a hypothesis of minimal force applied for the respiration, and the other data base relationship or the other data relationship can be based on a hypothesis of minimal work performed for the respiration. Since fundamentally it may be possible that the minimal force applied will also perform minimal work, for the hypothesis of minimal force applied, it should be precluded that the respiratory operating point determined thereby will also represent a minimum of applied respiration work. Likewise, for differentiation of the two hypotheses, in the case of a respiratory operating point determined from the hypothesis of a minimum of work performed in the respiration, it should be precluded that the force applied for the respiration is simultaneously also a minimum. In other words: the different hypotheses should provide different respiratory operating parameters for the same input quantities.

For the most precise determination of the respiratory operating parameter, according to an advantageous further development of the present invention, the first data base relationship or the first data relationship on the one hand, and the second data base relationship or the second data relationship on the other hand, each contains or preferably defines a relationship of one or a plurality of quantities of patient alveolar volume, patient respiratory organ dead-volume, patient respiratory path flow resistance, respiratory gas conduit arrangement flow resistance, patient respiratory organ compliance, respiratory gas conduit arrangement compliance and respiration frequency or derived or combined quantities of an individual or a plurality of the aforestated quantities. The first data relationship herein is different from the second data relationship, even if both data relationships contain the same quantities. As used herein, "contain" means that in addition to the quantities stated above, other quantities can be taken into account in the data relationship. "Defines" means herein that the particular data relationship is formed only from one or a plurality of the quantities named above.

The patient alveolar volume is that effective volume wherein gas exchange takes place between the respiratory gas introduced into the patient, and the blood of the patient. The patient respiratory organ dead volume is that volume of the respiratory organs of the patient to be ventilated, in which respiratory gas is indeed present, and said organs are also moved during the respiration, but the respiratory gas present in the dead volume is not involved in a gas exchange with the blood of the patient. The patient respiratory path flow resistance—preferably together with the respiratory gas conduit arrangement flow resistance—is the resistance determined individually for the particular respiratory case. The patient respiratory organ compliance—preferably together with the respiratory gas conduit arrangement compliance—is the compliance relevant to the particular respiratory case.

Thus a data base relationship comprised of a first and second data base relationship, or a data relationship of a first and second data relationship, can be a relationship of the quantities or data stated above pursuant to Mead. Also preferably the other data base relationship or data relationship can be a relationship of the quantities or data stated above pursuant to Otis. Not only have the Otis and Mead formulas proven themselves for decades in practice, they are additionally accepted world-wide, which is of decisive importance for the acceptance of a respiratory device among operating therapeutic personnel.

Basically it is possible to transfer or to input a patient respiratory organ part-volume, such as patient alveolar volume and/or the patient respiratory organ dead volume, over the existing data input into the control device. The same also applies to the respiratory gas requirement of the patient to be ventilated. Since a person's respiratory gas requirement is metabolized within the body, the respiratory gas requirement can be derived, for example, from the body weight of the particular patient. The patient's actual body weight can be used here, or an ideal body weight determined for the particular patient according to known rules (known as "ideal body weight"=IBW). Depending on the condition of the patient, the body weight used for determining the respiratory gas requirement can be multiplied by a coefficient in order to compute roughly a volume per minute.

Likewise, the patient respiratory organ dead volume can be determined in a known manner from the body weight, in particular from the ideal body weight referenced above, such as by multiplication with a coefficient defined specifically for this purpose.

The present invention will be explained in greater detail below with reference to the accompanying Figures.

Figure 2:
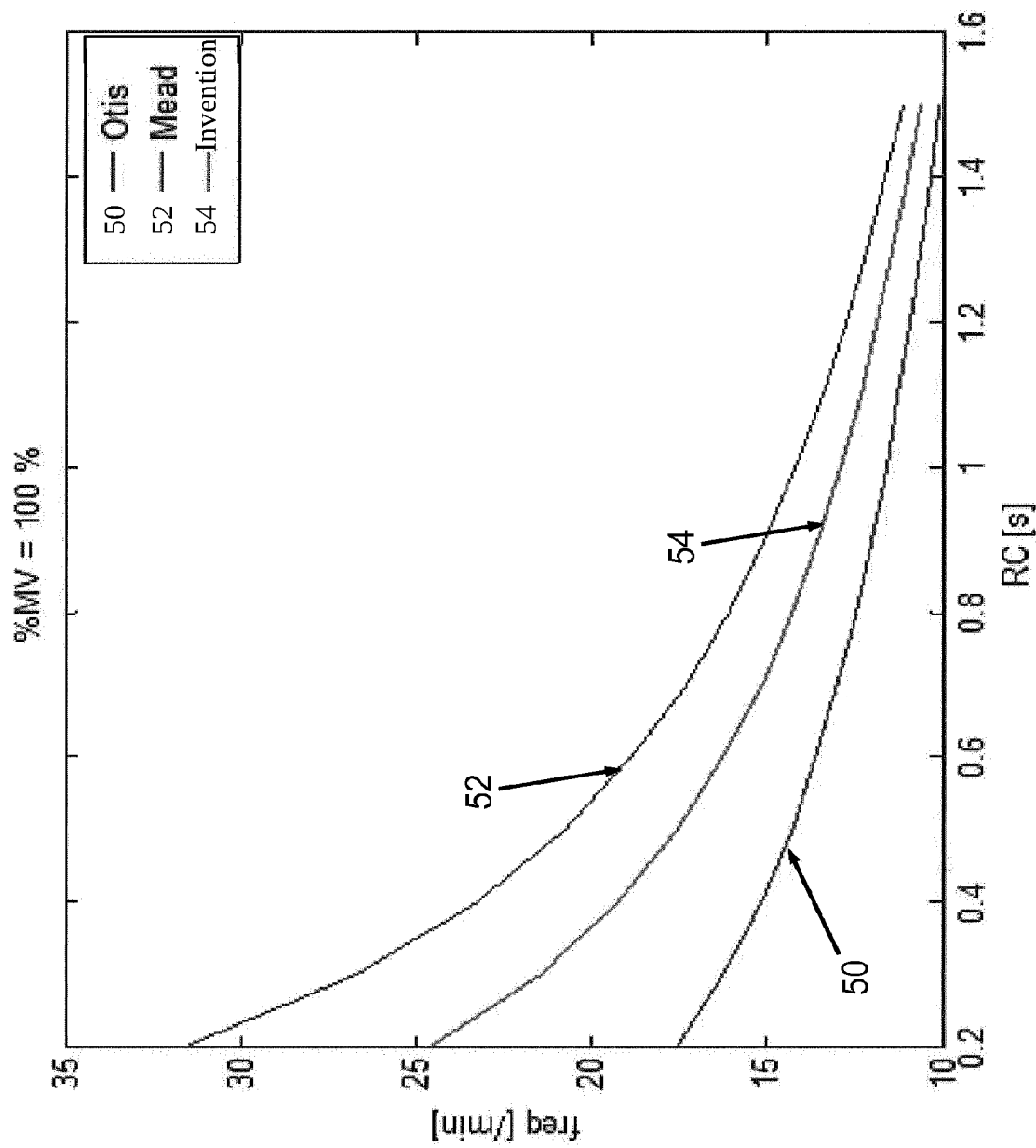
Figure 3:
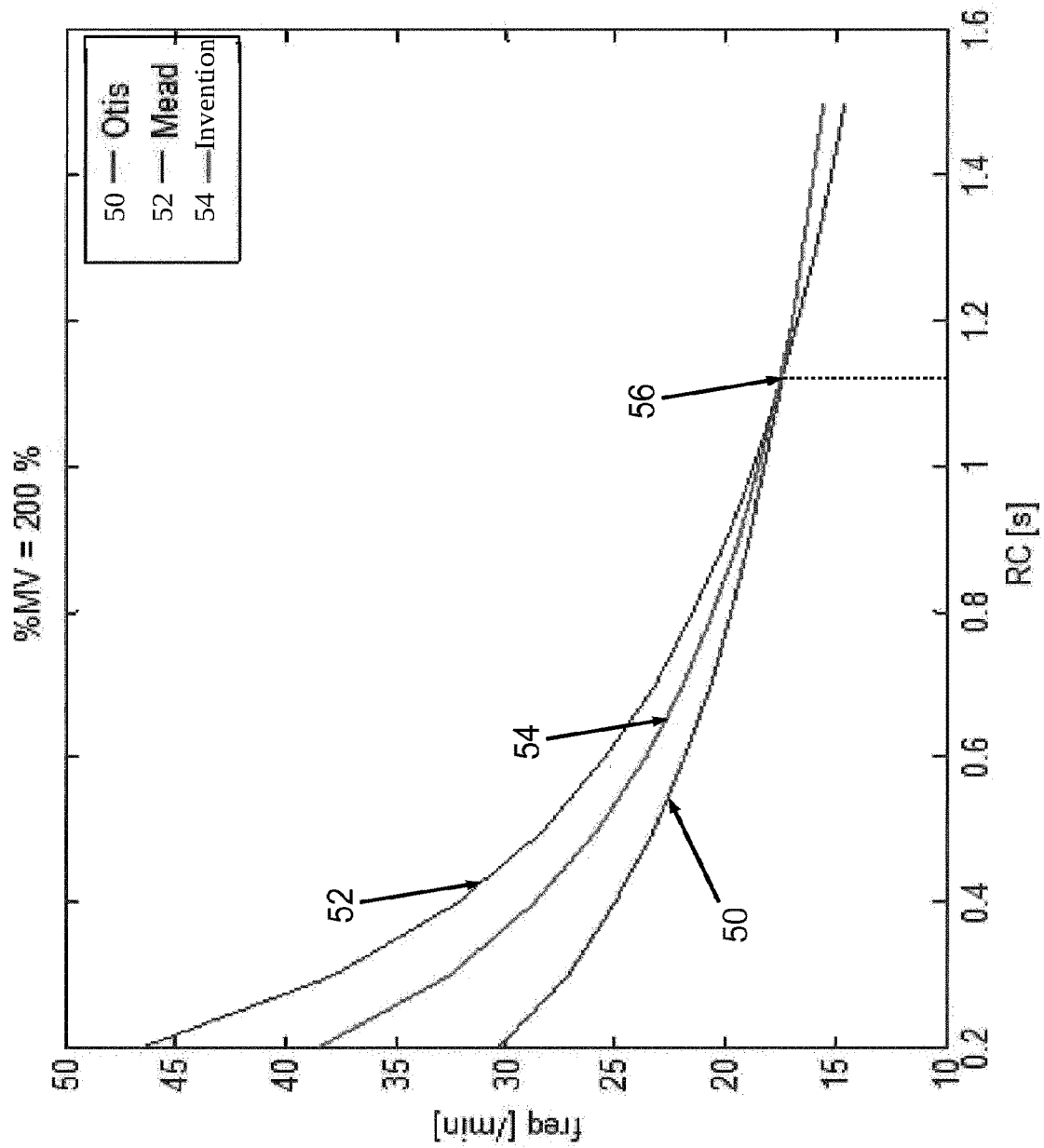
Figure 4:
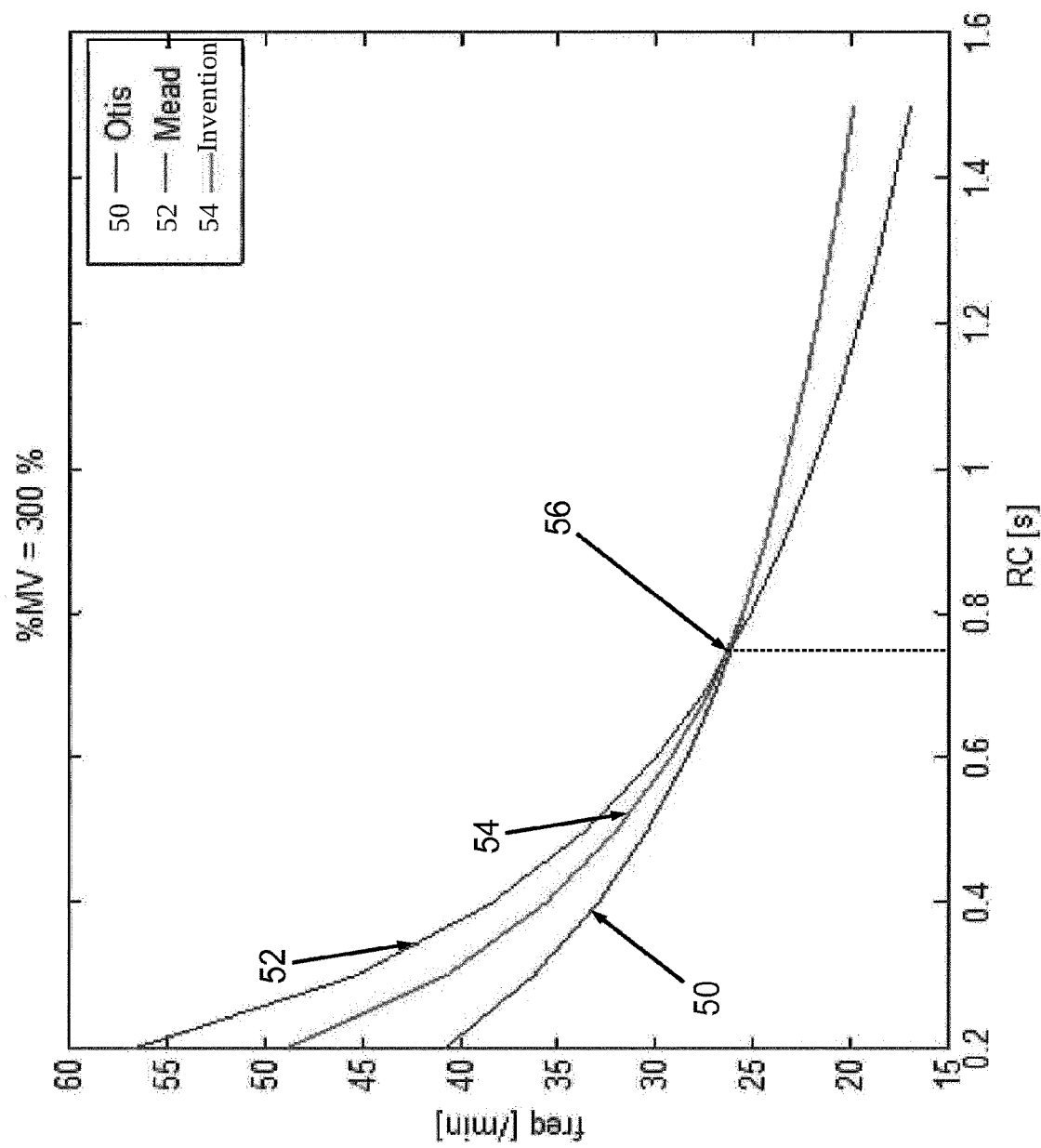

FIG. 1 depicts a schematic illustration of an inventive respiratory device configured for artificial respiration of a patient, FIG. 2 depicts an exemplary relationship of different values of the respiration-time constant and respiration frequency as respiration operating parameters, and comparative relationships pursuant to the formulas of Otis and Mead for a first respiratory gas requirement as used by the invented respiratory device, FIG. 3 depicts an exemplary relationship of different values of the respiration-time constant and respiration frequency as respiration operating parameters, and comparative relationships pursuant to the formulas of Otis and Mead for a second respiratory gas requirement as used by the inventive respiratory device, and FIG. 4 depicts an exemplary relationship of different values of the respiration-time constant and respiration frequency as respiration operating parameters, and comparative relationships pursuant to the formulas of Otis and Mead for a third respiratory gas requirement as used by the invented respiratory device.

FIG. 1 depicts an embodiment of a respiratory device according to the invention which is denoted in general by reference number 10. The respiratory device 10 in the illustrated example is used for artificial respiration of a human patient 12.

The respiratory device 10 includes a housing 14, wherein a pressure changing assembly 16 and a control device 18 can be accommodated—not externally visible due to the non-transparent housing material.

The pressure changing assembly 16 has a known design and can include a pump, a compressor, a fan, a pressure vessel, a reducing valve and the like. Furthermore, the respiratory device 10 includes an inspiration valve 20 and an exhalation valve 22 in a known manner.

The control device 18 is usually configured as a computer or microprocessor. It includes a storage device (not depicted in FIG. 1) to store, and to recall when necessary, the data needed for operation of the respiratory device 10. When operated on main power, the storage device can also be located outside of the housing 14 and be connected to the control device 18 by a data transmission link. The data transmission link can be formed by a cable or a wireless route.

However, to prevent disruptions in the data transmission link from having an effect on the operation of the respiratory device 10, the storage device is preferably integrated into the control device 18, or at least is accommodated in the same housing 14 therewith.

For input of data into the respiratory device 10, or more precisely into the control device 18, the respiratory device 10 has a data input 24, which is represented by a keyboard in the example depicted in FIG. 1. As will be explained below, the keyboard is not the sole data input to the control device 18. Actually, the control device 18 can receive data over different data inputs, such as over a network line, a wireless route or over sensor connectors 26, which will be discussed in greater detail below.

For output of data to the treating therapist, the respiratory device 10 can feature an output device 28, in the depicted example a screen.

For artificial respiration, the patient 12 is connected to the respiratory device 10, more precisely to the pressure changing assembly 16 in housing 14, via a respiratory gas conduit assembly 30. The patient 12 is intubated in this situation.

The respiratory gas conduit assembly 30 includes an inspiration tube 32 through which fresh respiratory gas can be supplied from the pressure changing assembly 16 into the lungs of the patient 12. The inspiration tube 32 can be interrupted and have a first inspiration tube 34 and a second inspiration tube 36, between them a conditioning device 38 can be provided for specific moistening and if necessary, temperature control of the fresh respiratory gas supplied to the patient 12. The conditioning device 38 can be connected to an external fluid reservoir 40 by which water for moisturizing, or even a medicine, such as an inflammation inhibitor or for expanding of the respiratory pathway, can be supplied to the conditioning device 38. When the present respiratory device IO is used as an anesthesia respiratory device, volatile anesthetics can be control-released to patient 12 via the respiratory device 10. The conditioning device 38 ensures that the fresh respiratory gas is supplied to the patient 12 with a predefined moisture content, if necessary, with addition of an aerosol medication, and at a predefined temperature.

The respiratory gas conduit assembly 30 features the already mentioned inspiration valve 20 and exhalation valve 22, and also an exhalation tube 42 through which metabolized respiratory gas is exhaled from the patient's 12 lungs into the atmosphere.

The inspiration tube 32 is connected to the inspiration valve 20; the exhalation tube 42 is connected to the exhalation valve 22. Of the two valves, only one is ever open for the passage of a gas stream. The actuation control of the valves 20 and 22 likewise takes place likewise using the control device 18.

During a respiration cycle, first the exhalation valve 22 is closed during the inspiration phase, and the inspiration valve 20 is opened, so that fresh respiratory gas can be directed from the housing 14 to the patient 12. A flow of the fresh respiratory gas is effected through a specific increase in pressure of the respiratory gas due to the pressure changing assembly 16. Due to the increased pressure, the fresh respiratory gas flows into the lungs of the patient 12 and there expands the near-lung region of the body, meaning in particular the chest cavity, against the individual elasticity of the near-lung parts of the body. Thus the gas pressure in the interior of the lungs of the patient 12 also increases.

At the end of the inspiration phase, the inspiration valve 20 is closed and the exhalation valve 22 is opened. The exhalation phase begins. Due to the elevated gas pressure of the respiration gas in the lungs of the patient 12 up until the end of the inspiration phase, after opening of the exhalation valve 22, this gas flows into the atmosphere, wherein as the duration of the flow increases, the gas pressure in the lungs of the patient 12 decreases. If the gas pressure in the lungs 12 reaches a positive final-exhalation pressure adjusted on the respiratory device 10, that is, a pressure slightly greater than atmospheric pressure, then the exhalation phase is completed with closure of the exhalation valve 22, and this is followed by an additional respiration cycle.

During the inspiration phase, the respiratory tidal volume is supplied to the patient 12, this is the respiratory gas volume per breath. The respiratory tidal volume multiplied by the number of respiration cycles per minute—e.g. multiplied by the respiratory frequency—yields the volume per minute of the implemented artificial respiration.

Preferably the respiratory device 10, in particular the control device 18, is configured to update or to ascertain repeatedly the respiratory operating parameters which characterize the respiratory operation of the respiratory device 10 during the respiratory operation in order to ensure that the respiratory operation at every point in time is optimally tailored as much as possible to the particular patient 12 to be ventilated. The determination of one or of several respiratory operating parameters with the respiratory frequency is particularly advantageous, so that for each respiratory cycle, updated respiratory operating parameters optimally adapted to the patient 12 can be obtained.

In this regard, the respiratory device 10 can be connected to one or several sensors for data transmission and which monitor the condition of the patient and/or the operation of the respiratory device. A flow sensor 44 is named in FIG. 1 solely as one example of a number of possible sensors; this sensor detects the respiratory gas flow prevailing in the respiratory gas conduit arrangement. The flow sensor 44 can be connected via a sensor conduit arrangement assembly 46 to the data inputs sensor connectors 26 of the control device 18. The sensor conduit assembly 46 can, but need not be composed of electrical signal transmission lines. It can likewise include tubing lines which transfer the gas pressure prevailing in the flow direction on both sides of the flow sensor 44 to the sensor connectors 26, where they are quantified by pressure sensors (not depicted in FIG. 1).

Solely for the sake of completeness, is it pointed out that the invented respiratory device 10 can be accommodated on a rolling frame 48 as a mobile respiratory device 10.

If the respiratory gas requirement of the patient 12 is known from the patient data—for example, calculated from the patient's 12 ideal body weight under consideration of the patient's disease picture—it is essential for a successful respiration of the patient 12 to divide the respiratory gas requirement, usually stated as a volume per minute or percent volume per minute, into individual breaths.

FIG. 2 presents three different data relationships for a percent volume per minute of 100% for the patient 12, which each denote a relationship between the respiratory time constant RC and a respiration frequency. The respiratory time constant RC is formed by the product of resistance and compliance. It indicates the respiratory resistance in connection with the patient 12. The respiratory frequency is an example of a respiratory operating parameter of the respiratory device 10.

The curve 50 has been determined on the basis of the known formula by Otis using a hypothesis of a minimum of respiratory work. Using a percent volume per minute of 100% for each realistic respiratory time constant value, it provides the lowest respiratory frequency and thus the greatest respiratory tidal volume, since the volume per minute is the product of respiratory frequency and respiratory tidal volume.

The curve 52 in FIG. 2 depicts a data relationship between the respiratory time constant RC and the respiratory frequency, which was determined according to the known formula of Mead on the basis of a hypothesis of a minimum of force applied for the respiration. This data relationship according to the Mead formula provides the greatest respiratory frequency and thus the smallest respiratory tidal volume for realistic respiratory time-constant values.

The respiratory device 10 according to the invention can be operated as follows: based on values obtained by sensors, for example, based on a time-correlated, cumulative measurement of the volume of respiratory gas in the exhalation phase, the current respiration time-constant value can be determined. This respiratory time-constant value according to the usual definition is that time period needed to exhale 63% of the respiratory tidal volume.

However, there are additional, alternative methods for determining the time constant for the case of artificial respiration. In this regard, reference is made to a paper by Brunner in "Critical Care Medicine" in the year 1995, or to Lourens in "Intensive Care Medicine" in the year 2000. The determination of an expiration time constant is proposed there as the quotient of a value of 75% of the exhalation tidal volume, divided by the exhalation flow which prevails at the moment when an exhalation volume of 75% of the exhalation tidal volume is reached.

With a current respiratory time-constant value determined in this way, the respiratory device 10, or more precisely the control device 18, determines a respiratory frequency according to Mead from curve 52 as a first respiratory base operating parameter and determines a respiratory frequency according to Otis from curve 50 as a second respiratory base operating parameter. The curves 50 and 52 are thus in the present example a second or a first data base relationship, respectively, according to the above description.

In the next step, the respiratory device 10, or more precisely the control device 18, compares the first respiratory base operating parameter, that is, the respiratory frequency according to Mead, to the second respiratory base operating parameter, that is, the respiratory frequency according to Otis. If the result of the comparison is that the first respiratory base operating parameter according to Mead is greater than the second respiratory base operating parameter according to Otis, then the respiratory device 10 determines the respiratory frequency as the respiratory operating parameter as an arithmetic average value of the respiratory frequencies according to Mead and to Otis:

$$Freq_{Invention} = \frac{freq_{Otis} + freq_{Mead}}{2} \quad (1)$$

However, if the respiratory frequency for the determined respiratory time-constant value according to Otis is greater than the respiratory frequency according to Mead, then the respiratory frequency according to Otis is selected as the respiratory base operating parameter.

In the example of FIG. 2, the respiratory frequency according to Otis is smaller than that per Mead for all realistically feasible respiratory time-constant values, so that the arithmetic average of the data relationships according to Otis and to Mead is always selected as the data relationship, and accordingly a respiratory frequency is determined for a known volume per minute and for a determined respiratory time-constant value. This data relationship is indicated in FIG. 2 as curve 54.

FIG. 3 depicts essentially the same database relationships of curves 50 and 52 for a percent volume per minute of 200%. Basically, the statements made above regarding FIG. 2 apply equally also to FIG. 3: first, in a known manner the present respiratory time-constant value RC is determined. A respiratory frequency is calculated for this respiratory time-constant value RC according to Mead and according to Otis. The obtained respiratory frequencies per Mead and per Otis are compared to each other. Then if the respiratory frequency per Mead is greater than that per Otis, the arithmetic average value of the two respiratory frequencies is calculated as the respiratory operating parameter according to the formula (I) provided above. If the respiratory frequency according to Otis is greater than that according to Mead, then the respiratory frequency per Otis is used as the respiratory operating parameter for operation of the respiratory device 10.

It is evident in FIG. 3 that the data base relationships of curves 50 and 52 intersect at a point of intersection 56 for a respiratory time-constant value of about 1.12 s. Thus, left of the point of intersection 56, that is, for respiratory time-constant values of less than 1.12 s, the respiration frequency calculated per Mead for each respiratory time-constant value is greater than that per Otis, so that for this range of respiratory time-constant values less than 1.12 s, the above formula (1) will always be applied for the determination of the respiratory frequency to be adjusted on the respiratory device 10 as respiratory operating parameter.

For respiratory time-constant values greater than 1.12 s however, the opposite is always the case: here the respiratory frequency per Otis, calculated for each respiratory time-constant value, is always greater than that per Mead, so that for this range of respiratory time-constant values, the Otis respiratory frequency is always used or adjusted on the respiratory device 10 as respiratory operating parameter. The point of intersection 56 is a threshold resistance data value like that stated above in the descriptive introduction.

FIG. 4 shows essentially the same fundamental data relationships or data base relationships as in FIGS. 2 and 3, but for a percent volume per minute of 300%, that is, for a greatly elevated respiratory gas requirement. The discussion of FIG. 3 applies *mutatis mutandis* to FIG. 4, with the proviso that the point of intersection or threshold resistance data value 56 is located at a respiratory time-constant value of 0.75 s for the respiratory gas requirement relevant to FIG. 4.

With the respiratory device 10 according to the present invention, the artificial respiration carried out on patients 12 can be better adapted than before to the actual patient and his condition. Since both the calculation method per Otis and also the calculation method per Mead continue to be recognized and accepted, then also a value which is disposed between the results of the two recognized calculation methods cannot fail to be recognized for its applicability. Because if each of the respiratory operating parameters obtained from Otis and Mead is therapeutically suitable for a respiratory time-constant value and for a specific respiratory gas requirement, then also a new respiratory operating parameter located between these known respiratory operating parameters must also be therapeutically suitable.

The invention claimed is:

1. A respiratory device for the at least supportive-partial artificial respiration of patients, comprising:
   a respiratory gas conduit assembly,
   a pressure changing assembly for changing the pressure of respiratory gas in the respiratory gas conduit assembly during the respiratory operation of the respiratory device; and
   a control device controlling the respiratory operation of the pressure changing assembly such that the patient is supplied with a predetermined respiratory gas volume per minute;
   wherein the control device has a data input for transmitting operational and/or patient data to the control device;

wherein the control device is configured to determine a respiration tidal volume or a respiration frequency as a respiratory operating parameter for the operation of the pressure changing assembly selectively using a predetermined first data relationship or using a predetermined second data relationship that is different from the first data relationship;

wherein the control device is configured to select a data relationship from the predetermined first and the predetermined second data relationship depending on a resistance data value denoting a respiration resistance in connection with a patient to be ventilated, and thus to determine the respiratory operating parameter for the predetermined respiratory gas volume per minute according to the selected data relationship from the first data relationship and the second data relationship using at least one calculation step;

wherein the resistance data value takes into account at least one of (1) a flow resistance value of at least one of (a) the respiratory path of the patient to be ventilated and (b) the respiration gas conduit assembly, and (2) a flexibility value of at least one of (a) the respiration organs of the patient to be ventilated and (b) the respiration gas conduit assembly.

2. The respiratory device according to claim 1, wherein the respiratory device is configured to determine the resistance data value.

3. The respiratory device according to claim 2, wherein the respiratory device is configured to be connected for the purpose of data transmission to one or more sensors to determine operating parameters of the pressure changing arrangement and/or of the respiratory gas conduit assembly.

4. The respiratory device according to claim 1, wherein the respiratory device is configured to determine a first respiratory base operating parameter for a resistance data value according to a predetermined, first data base relationship and to determine a second respiratory base operating parameter according to a predetermined, second data base relationship different from the first, wherein the respiratory device is further configured to compare the first and the second respiratory base operating parameters with each other, and depending on the result of the comparison, to determine the respiratory operating parameter using the predetermined, first data relationship or using the predetermined, second data relationship.

5. The respiratory device according to claim 4, wherein the respiratory device is configured such that when the first respiratory base operating parameter is greater than the second respiratory base operating parameter, an average value, of the first and of the second respiratory base operating parameter is used as the respiratory operating parameter, and when the first respiratory base operating parameter is less than the second respiratory base operating parameter or is equal to the second respiratory base operating parameter, the second respiratory base operating parameter is used as the respiratory operating parameter.

6. The respiratory device according to claim 4, wherein the first data relationship is a function of forming an average value of the first and the second data base relationship.

7. The respiratory device according to claim 6, wherein the function of forming an average value is an arithmetic average value.

8. The respiratory device according to claim 4, wherein the respiratory device is configured such that when the first respiratory base operating parameter is greater than the second respiratory base operating parameter, an arithmetic average value of the first and of the second respiratory base operating parameter is used as the respiratory operating parameter, and when the first respiratory base operating parameter is less than the second respiratory base operating parameter or is equal to the second respiratory base operating parameter, the second respiratory base operating parameter is used as the respiratory operating parameter.

9. The respiratory device according to claim 1, wherein for at least a portion of the respiratory gas requirements selectable and/or adjustable on the respiratory device, there exists one threshold resistance data value each, wherein the control device is configured such that when the resistance data value of the patient to be ventilated is below the threshold resistance data value, the respiratory device determines the respiration operating parameter according to the first data relationship, and when the resistance data value of the patient is above the threshold resistance data value, the respiratory device determines the respiration operating parameter according to the second data relationship.

10. The respiratory device according to claim 9, wherein when the operating and patient data for the threshold resistance data value are otherwise equal, then the first and the second data relationship cause the determination of a same value for the respiration operating parameter.

11. The respiratory device according to claim 1, wherein the first data base relationship or the first data relationship on the one hand, and the second data base relationship or the second data relationship on the other hand, each contains or defines a relationship of individual or a plurality of quantities of patient alveolar volume, patient respiratory organ dead-volume, patient respiratory path flow resistance, patient respiratory organ compliance, respiratory gas conduit arrangement flow resistance, respiratory gas conduit arrangement compliance and respiration frequency or derived or combined quantities of individual or a plurality of the aforestated quantities.

12. The respiratory device according to claim 1, wherein the control device is configured to determine a patient respiratory organ part volume and/or a respiratory gas requirement, depending on patient data of a patient to be ventilated.

13. The respiratory device according to claim 12, in that wherein the control device is configured to determine a patient respiratory organ dead volume as a function of an ideal body weight of the patient to be ventilated and/or is configured to determine a respiratory gas volume per minute as a function of an ideal body weight of the patient to be ventilated.

14. The respiratory device according to claim 1, wherein the control device for controlling the respiratory operation of the respiratory device controls the pressure changing assembly, wherein the respiratory operating parameter is for the operation of the pressure changing assembly.

15. The respiratory device according to claim 1, wherein the respiratory device is configured to determine the resistance data value repeatedly.

16. The respiratory device according to claim 1, wherein the respiratory device is configured to determine the resistance data value after each or for each respiratory cycle.

17. The respiratory device according to claim 1, wherein for at least a portion of the respiratory gas requirements selectable and/or adjustable on the respiratory device, there exists one threshold resistance data value each, wherein the control device is configured such that when the resistance data value of the patient to be ventilated is below the threshold resistance data value, the respiratory device determines the respiration operating parameter in the form of a function of a first and/or of a second data base relationship, and when the resistance data value of the patient is above the threshold resistance data value, the respiratory device determines the respiration operating parameter according to the second data relationship.

18. The respiratory device according to claim 1, wherein for at least a portion of the respiratory gas requirements selectable and/or adjustable on the respiratory device, there exists one threshold resistance data value each, wherein the control device is configured such that when the resistance data value of the patient to be ventilated is below the threshold resistance data value, the respiratory device determines the respiration operating parameter in the form of a function of a first and/or of a second data base relationship, and when the resistance data value of the patient is above the threshold resistance data value, the respiratory device determines the respiration operating parameter in the form of a function of a first and/or of a second data base relationship.

19. The respiratory device according to claim 1, wherein the respiration gas requirement is a stated in percent volume per minute.

20. The respiratory device according to claim 1, wherein the resistance data value takes into account a flow resistance value of the respiratory path of the patient to be ventilated and/or of the respiration gas conduit assembly, and/or a flexibility value of the respiration organs of the patient to be ventilated and/or of the respiration gas conduit assembly wherein the resistance data value takes into account a respiration time-constant formed by the product of flow resistance value and flexibility value in connection with the patient to be ventilated.

21. The respiratory device according to claim 1, wherein the resistance data value takes into account a flow resistance value of the respiratory path of the patient to be ventilated and/or of the respiration gas conduit assembly, and/or a flexibility value of the respiration organs of the patient to be ventilated and/or of the respiration gas conduit assembly wherein the resistance data value takes into account a respiration time-constant formed by the product of flow resistance value and flexibility value in connection with the patient to be ventilated, and is the respiration-time constant.

22. The respiratory device according to claim 1, wherein the first data base relationship or the first data relationship on the one hand, and the second data base relationship or the second data relationship on the other hand, each contains or defines a relationship of individual or a plurality of quantities of patient alveolar volume, patient respiratory organ dead-volume, patient respiratory path flow resistance, patient respiratory organ compliance, respiratory gas conduit arrangement flow resistance, respiratory gas conduit arrangement compliance and respiration frequency or derived or combined quantities of individual or a plurality of the aforestated quantities, wherein the first data base relationship or the first data relationship is a relationship of the stated data pursuant to Mead.

23. The respiratory device according to claim 1, wherein the first data base relationship or the first data relationship on the one hand, and the second data base relationship or the second data relationship on the other hand, each contains or defines a relationship of individual or a plurality of quantities of patient alveolar volume, patient respiratory organ dead-volume, patient respiratory path flow resistance, patient respiratory organ compliance, respiratory gas conduit arrangement flow resistance, respiratory gas conduit arrangement compliance and respiration frequency or derived or combined quantities of individual or a plurality of the aforestated quantities, wherein the second data base relationship or the second data relationship is a relationship of the stated data pursuant to Otis.

24. The respiratory device according to claim 1, wherein the control device is con-figured to determine the respiratory operating parameter for the predetermined respiratory gas volume per minute according to the selected data relationship from the first data relationship and the second data relationship using a plurality of calculation steps.

25. A respiratory device for the at least supportive-partial artificial respiration of patients, comprising:
a respiratory gas conduit assembly;
a pressure changing assembly for changing the pressure of respiratory gas in the respiratory gas conduit assembly during the respiratory operation of the respiratory device; and
a control device controlling the respiratory operation of the pressure changing assembly such that the patient is supplied with a predetermined respiratory gas volume per minute;
wherein the control device has a data input for transmitting operational and/or patient data to the control device;
wherein the control device is configured to determine a respiration tidal volume or a respiration frequency as a respiratory operating parameter for the operation of the pressure changing assembly selectively using a predetermined first data relationship or using a predetermined second data relationship that is different from the first data relationship;
wherein the control device is configured to select a data relationship from the predetermined first and the predetermined second data relationship depending on a resistance data value denoting a respiration resistance in connection with a patient to be ventilated, and thus to determine the respiratory operating parameter for the predetermined respiratory gas volume per minute according to the selected data relationship from the first data relationship and the second data relationship,
wherein the respiratory device is configured to determine a first respiratory base operating parameter for a resistance data value according to a predetermined, first data base relationship and to determine a second respiratory base operating parameter according to a predetermined, second data base relation-ship different from the first, wherein the respiratory device is further configured to compare the first and the second respiratory base operating parameters with each other, and depending on the result of the comparison, to determine the respiratory operating parameter using the predetermined, first data relationship or using the predetermined, second data relationship.

* * * * *